United States Patent [19]

Cairns et al.

[11] 4,239,748

[45] Dec. 16, 1980

[54] INORGANIC SALTS OF 2,8-DICARBOXY-4,6-DIOXO-10-PROPYL-4H,6H-BENZO(1,2-b:5,4-b')DIPYRAN USEFUL FOR THE TREATMENT OF ASTHMA AND HAY FEVER

[75] Inventors: Hugh Cairns; Kenneth Brown, both of Loughborough; Roger E. C. Altouyan, Wilmslow, all of England

[73] Assignee: Fisons Limited, London, England

[21] Appl. No.: 963,813

[22] Filed: Nov. 27, 1978

[30] Foreign Application Priority Data

Nov. 30, 1977 [GB] United Kingdom ............... 49764/77

[51] Int. Cl.$^2$ ...................... A61L 9/04; A61K 31/35; C07D 311/78
[52] U.S. Cl. .................................. 424/45; 260/345.2; 424/283
[58] Field of Search ...................... 260/345.2; 424/283, 424/45

[56] References Cited

U.S. PATENT DOCUMENTS

| | | | |
|---|---|---|---|
| 3,673,218 | 6/1972 | Cairns et al. | 260/345.2 |
| 3,686,320 | 8/1972 | Fitzmaurice et al. | 260/345.2 |
| 3,718,668 | 2/1973 | Cairns et al. | 260/345.2 |

OTHER PUBLICATIONS

Bantick et al., J. Med. Chem., 19, 817 (1976).

*Primary Examiner*—Nicky Chan
*Attorney, Agent, or Firm*—Merriam, Marshall & Bicknell

[57] ABSTRACT

There is described a salt of 2,8-dicarboxy-4,6-dioxo-10-propyl-4H,6H-benzo(1,2-b:5,4-b')dipyran with a pharmaceutically acceptable inorganic cation, the salt having a solubility of less than 3% w/w in water a 20.5° C.

There are also described processes for making the salts and pharmaceutical, e.g. anti-allergic, compositions containing them.

12 Claims, No Drawings

INORGANIC SALTS OF 2,8-DICARBOXY-4,6-DIOXO-10-PROPYL-4H,6H-BENZO(1,2-b:5,4-b')DIPYRAN USEFUL FOR THE TREATMENT OF ASTHMA AND HAY FEVER

This invention relates to new salts, methods for their preparation and use, and compositions containing them.

Disodium cromoglycate has for many years been known to be of use in the prophylactic treatment of allergic asthma. However disodium cromoglycate has the disadvantage that, while having considerable duration of action, its duration of action is sometimes insufficient to enable the patient to obtain a full night's sleep. Furthermore disodium cromoglycate, while providing useful protection, usually provides less than 100% protection, against asthma. The dosage of disodium cromoglycate usually administered for asthma is also relatively large. A number of other compounds, including certain benzodipyran dicarboxylic acids, have also been suggested for prophylactic use in the treatment of asthma. However no compound other than disodium cromoglycate has yet been successfully sold for this purpose, either because of lack of efficacy or the presence of undesirable side effects, e.g. bronchoconstriction.

We have now found that certain salts of a particular compound possess advantageous properties.

According to the invention we provide a salt of 2,8-dicarboxy-4,6-dioxo-10-propyl-4H,6H-benzo(1,2-b:5,4-b')dipyran with a pharmaceutically acceptable inorganic cation, the salt having a solubility of less than 3%, preferably less than 2%, more preferably less than 1% and most preferably less than 0.5% w/w in water at 20.5° C.

The cation may be a di- or tri-basic inorganic cation and may be a cation of a metal in group II of the Periodic Table, for example magnesium or preferably calcium. Other inorganic cations which may be mentioned include zinc and iron.

The salt may be a salt of one or both of the carboxylic acid groups of the 2,8-dicarboxy-4,6-dioxo-10-propyl-4H,6H-benzo(1,2-b:5,4-b')dipyran. The alkali metal salts of 2,8-dicarboxy-4,6-dioxo10-propyl-4H,6H-benzo-(1,2-b:5,4-b')dipyran do not form part of the present invention.

The salt may be made by a metathetical process, e.g. by reacting a solution of a suitable salt, such as the sodium salt, of 2,8-dicarboxy-4,6-dioxo-10-propyl-4H,6H-benzo(1,2-b:5,4-b')dipyran with an appropriate solution containing the required cation in available form. The salt used as starting material may, if desired, have been formed in situ, e.g. by hydrolysis of the corresponding ester, and need not be isolated before use in the metathetical process. The required salt may also be produced by reacting the free acid, 2,8-dicarboxy-4,6-dioxo-10-propyl-4H,6H-benzo-(1,2-b:5,4-b')dipyran, or a suitable ester or amide thereof, e.g. a C 1 to 10 alkyl ester, or a mono- or di- C 1 to 10 amide or an amide derived from ammonia, with a base containing the required cation in available form. The reaction may be carried out in a solvent which is inert under the reaction conditions. The solvent is preferably one in which the desired salt is relatively insoluble, e.g. water. The desired salt may be isolated and purified, for example by filtration and/or crystallisation.

The 2,8-dicarboxy-4,6-dioxo-10-propyl-4H,6H-benzo(1,2-b:5,4-b')-dipyran may be made from known compounds using techniques known per se. We prefer the 10-propyl group to be an n-propyl group.

The salts according to the invention are useful because they possess pharmacological activity in animals; in particular they are useful because they inhibit the release and/or action of pharmacological mediators which result from in vivo combination of certain types of antibody and specific antigen e.g. the combination of reaginic antibody with specific antigen. In man, both subjective and objective changes which result from the inhalation of specific antigen by sensitised subjects are inhibited by prior administration of the new salts. Thus the new salts are useful in the treatment of asthma, e.g. allergic asthma. The new salts are also useful in the treatment of so-called 'intrinsic' asthma (in which no sensitivity to extrinsic antigen can be demonstrated). The new salts are also of value in the treatment of other conditions in which antigen-antibody reactions are responsible for disease, for example, hay fever and urticaria.

For the above mentioned uses the dosage administered will, of course, vary with the salt employed, the mode of administration and the treatment desired. However, in general, satisfactory results are obtained when the salts are administered at a dosage of from 0.01 to 5 mg per kg of animal body weight in the test set out in Example 27 of British Patent Specification No. 1,292,601. For man the indicated total daily dosage is in the range of from 0.1 mg to 1,000 mg, preferably from 0.3 mg to 100 mg and more preferably from 0.5 mg to 50 mg, which may be administered in divided doses from 1 to 3 times a day. Thus unit dosage forms suitable for administration (e.g. by inhalation) comprise from 0.1 mg to 1,000 mg, preferably 0.15 mg to 100 mg and more preferably from 0.15 mg to 50 mg of the salt preferably admixed with a solid or liquid pharmaceutically acceptable diluent, carrier or adjuvant. When hay fever is to be treated, lower unit doses, e.g. of from 0.1 to 1 mg, administered from 1 to 8 times a day may be used.

The salts according to the invention have the advantage that they are more efficacious or more potent in certain pharmacological models, or are less rapidly absorbed, or are longer acting, e.g. as measured by duration of action studies in experimental asthma in a human volunteer, or cause fewer (or less marked) undesirable side effects, e.g. bronchoconstriction when administered by inhalation than disodium cromoglycate or the free acid 2,8-dicarboxy-4,6-dioxo-10-propyl-4H,6H-benzo(1,2-b:5,4-b')-dipyran or its disodium salt.

According to our invention we also provide a pharmaceutical composition comprising (preferably less than 80%, more preferably less than 50% and most preferably less than 5% by weight) of a salt according to the invention, in combination with a pharmaceutically acceptable adjuvant, diluent or carrier. Examples of suitable adjuvants, diluents or carriers are:- for tablets capsules and dragees; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; and for inhalation compositions, a coarse carrier, e.g. lactose, or propellant liquified gases, e.g. propellant 12, propellant 11, propellant 114 or a mixture of two or more thereof, and a surfactant, e.g. a sorbitan ester, such as sorbitan trioleate. The salt is preferably in a form having a mass median diameter of from 0.01 to 10 microns. The compositions may also contain suitable preserving, stabilising and wetting agents, solubilizers, sweetening and colouring agents and flavourings. The compositions may, if desired, be formulated in sustained release form. We prefer compositions which are designed to be taken by nasal or oral inhalation.

The calcium and magnesium salts can form hydrates; thus the calcium salt forms a stable tri-hydrate and the magnesium salt forms a stable tetra-hydrate.

The invention is illustrated, but in no way limited by the following Examples. Example 3 relates to the free acid and does not illustrate a salt of the invention.

EXAMPLE 1

Calcium 4,6-dioxo-10-propyl-4H,6H-benzo[1,2-b:5,4-b']dipyran2,8-dicarboxylate

A solution of calcium nitrate (2.0 g) in water (25 ml) was added to a solution of disodium 4,6-dioxo-10-propyl-4H,6H-benzo[1,2-b:5.4-b']dipyran-2,8-dicarboxylate (2.3 g) in water (25 ml) and the mixture was stirred for 30 minutes at room temperature. The precipitate was filtered off, washed well with water and ethanol and dried in vacuo at 70° C. to give the required calcium salt (1.7 g; 77%), m.p.>300° C.

$C_{17}H_{10}CaO_8$ requires: C: 53.4, H: 2.6%;
found: C: 46.7, H: 3.7%;
contains 12.55% water.

EXAMPLE 2

Magnesium 4,6-dioxo-10-propyl-4H,6H-benzo-[1,2-b:5,4-b']dipyran-2,8-dicarboxylate A solution of magnesium chloride hexahydrate (12 g) in water (10 ml) was added to a solution of disodium 4,6-dioxo-10-propyl-4H,6H-benzo[1,2-b:5,4-b']dipyran-2,8-dicarboxylate (2.0 g) in water (15 ml) and the mixture was stirred for 30 minutes at room temperature. The precipitate was filtered off and washed well with water. The solid was stirred with acetone, filtered off and dried in vacuo at 70° C. to give the required magnesium salt (1.0 g; 53%) m.p. 300° C.

$C_{17}H_{10}MgO_8$ requires: C: 55.7, H: 2.75%;
found: C: 46.7, H: 4.3%;
contains 16.2% water.

EXAMPLE 3

4,6-Dioxo-10-propyl-4H,6H-benzo[1,2-b:5,4-b']dipyran-2,8-dicarboxylic acid monohydrate To a solution of 2-propyl resorcinol (18.3 g) and dimethylacetylenedicarboxylate (34 g) in ethanol (500 ml) was added benzyltrimethyl ammonium hydroxide (2 ml) and the resulting red mixture was heated to reflux for 20 hours. This solution was cooled, and to it was added a solution of sodium hydroxide (30 g) in water (150 ml), and the whole was heated to reflux for 2 hours. After cooling the reaction mixture was poured into water (2 liter) and repeatedly washed with ethyl acetate. The aqueous solution was acidified with concentrated hydrochloric acid, and the resulting precipitate was collected, washed well with water and dried in vacuo at 80° C. to afford a cream solid (21 g).

The dried solid (21 g) was added to the chlorosulphonic acid (200 ml) cooled in an ice-bath, in portions at such a rate that the reaction temperature did not rise above 10° C., and when addition was complete the reaction was heated to 50° C. for 2½ hours. The reaction mixture was cooled and poured into ice/water (3 liter), and the resultant precipitate was collected, washed well with water and dried in vacuo. The dried solid was boiled with ethanol (100 ml), the insoluble material was collected and boiled with ethyl acetate (100 ml), and the remaining insoluble material was collected by centrifugation. Drying in vacuo at 60° C. afforded the title compound as a brown solid (10.5 g).

Found: C, 56.6% H, 3.8%
$C_{17}H_{12}O_8 \cdot H_2O$ requires: C, 56.36% H, 3.89%

EXAMPLE A

| | Pressurised Aerosol Formulation Percentage by weight of: | | | | |
|---|---|---|---|---|---|
| No | Salt of Example 1 | Sorbitan Trioleate | Propellant 11 | Propellant 114 | Propellant 12 |
| 1. | 0.0715 | 0.2000 | 39.8914 | — | 59.8371 |
| 2. | 0.0715 | 0.0500 | 39.9514 | — | 59.9271 |
| 3. | 0.1430 | 0.2000 | 39.8628 | — | 59.7942 |
| 4. | 0.2260 | 0.1581 | 39.8463 | — | 59.7696 |
| 5. | 0.3574 | 0.2500 | 39.7570 | — | 59.6356 |
| 6. | 0.7148 | 0.5000 | 39.5141 | — | 59.2711 |
| 7. | 1.4296 | 1.0000 | 39.0282 | — | 58.5422 |
| 8. | 0.1442 | 0.0100 | — | 39.9383 | 59.9075 |
| 9. | 0.1442 | 0.0200 | — | 39.9343 | 59.9015 |
| 10. | 0.1442 | 0.0500 | — | 39.9223 | 59.8835 |
| 11. | 0.1413 | 0.0500 | — | 59.8852 | 39.9235 |
| 12. | 0.3605 | 0.1250 | — | 39.8058 | 59.7087 |
| 13. | 0.7210 | 0.2500 | — | 39.6116 | 59.4174 |

Methods of preparation (a) formulations 1 to 7

Dissolve the sorbitan trioleate in the propellant 11, add the drug and disperse using a high-shear mixer. Cool to −50° C., add the propellant 12 at −50° C. and mix thoroughly. Fill into aerosol vials, valve and crimp.

(b) formulations 8 to 13

Disperse the sorbitan trioleate in the propellant 12 at −50° C. using a high-shear mixer. Add the drug and disperse. Add the propellant 114 at −50° C. and mix thoroughly. Fill into aerosol vials, valve and crimp.

The preferred formulations are those of numbers 10 to 13, formulation number 11 being particularly suitable for nasal application.

Example B

Inhalation powder formulations (a) for oral administration

| | Percentage by weight |
|---|---|
| Salt of Example 1 particle size less than 10 microns | 1.67 |
| Coarse lactose particle size less than 200 microns | 98.33 |

Method

Intimately mix the drug with the coarse lactose (preferably substantially in the particle size range 30 to 80 μm). Fill into No 2 hard gelatin capsules with a target fill weight of 30 mg. This will give 0.5 mg of drug per capsule. Administer using a powder inhalation device.

(b) for nasal administration

|  | percentage by weight |
| --- | --- |
| Salt of Example 1 particle size less than 10 microns | 0.83 |
| Coarse lactose particle size less than 200 microns | 99.17 |

Method

As above, fill into No 3 hard gelatin capsules, target fill weight 30 mg to give 0.25 mg of drug per capsule. Administer one capsule to each nostril using a nasal insufflator.

Example C

The activity of the new salts of 2,8-dicarboxy-4,6-dioxo-10-propyl-4H,6H-benzo(1,2:5,4-b')dipyran has been evaluated by the antigen inhalation test on human volunteers who suffer from specific allergic asthma. The degree of asthma provoked by the inhalation of an antigen to which the volunteers are sensitive can be measured by repeated estimation of the increase of airway resistance.

A suitably designed spirometer was used to measure the forced expiratory volume at one second ($F.E.V._1$) and hence the changes in the air way resistance. The anti-allergic activity of a salt is estimated from the difference between the maximum percent $F.E.V._1$ reduction following control and test provocations after drug administration conducted under identical experimental conditions.

Thus:

$$\% \text{ protection} = 100 \times \left[ \frac{\text{Av.max } \% \ F.E.V_1\text{-max } \% \ F.E.V._{1.0} \text{ fall control shock fall test shock}}{\text{Av. max } \% \ F.E.V_{1.0} \text{ fall control shock}} \right]$$

The salts under test were administered by inhalation (as a pressurised aerosol formulation of the type described in Example A) at the desired time before challenge with antigen.

We claim:

1. A salt of 2,8-dicarboxy-4,6-dioxo-10-propyl-4H,6H-benzo(1,2-b:5,4-b')dipyran with a pharmaceutically acceptable inorganic cation, the salt having a solubility of less than 3% w/w in water at 20.5° C.

2. A salt according to claim 1, which is less than 2% w/w soluble in water at 20.5° C.

3. A salt according to claim 2, which is less than 1% w/w soluble in water at 20.5° C.

4. A salt according to claim 3 which is less than 0.5% w/w soluble in water at 20.5° C.

5. A salt according to claim 1, wherein the cation is a dibasic inorganic cation.

6. A salt according to claim 1, which is calcium 4,6-dioxo-10propyl-4H,6H-benzo[1,2-b:5,4-b']dipyran-2,8-dicarboxylate.

7. A salt according to claim 6, which is calcium 4,6-dioxo-10-propyl-4H,6H-benzo[1.2-b:5,4-b']dipyran-2,8-dicarboxylate trihydrate.

8. A salt according to claim 1, which is magnesium 4,6-dioxo-10-propyl-4H,6H-benzo[1,2-b:5,4-b']dipyran-2,8-dicarboxylate.

9. A pharmaceutical composition for treatment of asthma or hay fever comprising an effective proportion of a salt according to claim 1, as active ingredient, in combination with a pharmaceutically acceptable adjuvant, diluent or carrier.

10. A composition according to claim 9 in a dry powder form suitable for inhalation and comprising coarse lactose.

11. A composition according to claim 9 in a form suitable for inhalation and comprising a propellant liquified gas and a surfactant.

12. A method of treatment of asthma or hay fever, which comprises administration of a salt according to claim 1 to a patient suffering from such a condition.

* * * * *